United States Patent [19]
Schulman et al.

[11] Patent Number: 5,358,514
[45] Date of Patent: Oct. 25, 1994

[54] IMPLANTABLE MICRODEVICE WITH SELF-ATTACHING ELECTRODES

[75] Inventors: Joseph H. Schulman, Santa Clarita; Primoz Strojnik, Granada Hills; Paul Meadows, Altadena, all of Calif.

[73] Assignee: Alfred E. Mann Foundation for Scientific Research, Sylman, Calif.

[21] Appl. No.: 62,283

[22] Filed: May 17, 1993

Related U.S. Application Data

[63] Continuation-in-part of Ser. No. 25,994, Mar. 3, 1993, which is a continuation of Ser. No. 812,051, Dec. 18, 1991, Pat. No. 5,193,540.

[51] Int. Cl.$^5$ ............................................. A61N 1/36
[52] U.S. Cl. ...................................... 607/61; 607/118
[58] Field of Search ................................ 607/60–61, 607/118

[56] References Cited

U.S. PATENT DOCUMENTS

| | | | |
|---|---|---|---|
| 3,646,940 | 3/1972 | Timm et al. | 128/421 |
| 4,006,748 | 2/1977 | Schulman | 128/419 P |
| 4,026,300 | 5/1977 | DeLuca et al. | 128/418 |
| 4,026,303 | 5/1977 | Babotai | 128/418 |
| 4,198,991 | 4/1980 | Harris | 128/484 |
| 4,333,072 | 6/1982 | Beigel | 340/825 |
| 4,524,774 | 6/1985 | Hildebrandt | 128/421 R |
| 4,573,481 | 3/1986 | Bullara | 128/784 |
| 4,590,946 | 5/1986 | Loeb | 128/642 |
| 4,602,624 | 7/1986 | Naples et al. | 128/784 |
| 4,679,560 | 7/1987 | Galbraith | 128/419 R |
| 4,763,656 | 8/1988 | Nauman | 128/421 |
| 4,920,979 | 5/1990 | Bullara | 128/784 |
| 4,934,368 | 6/1990 | Lynch | 128/419 R |

OTHER PUBLICATIONS

Guyton, et al., "Theory and Design of Capacitor Electrodes for Chronic Stimulation", *Medical and Biological Engineering*, vol. 12 pp. 613–619 (Sep. 1974).

Hildebrandt, et al., "Neuromuscular Functional Stimulation by Miniaturized implantable Electric Stimulators", *Proceedings of the Seventh International Symposium on External Control of Human Extremities*, Dubrovnik, Yugoslavia (Sep. 7–12, 1981).

An article in *CRC Reviews in Bioengineering* (Sep. 1981).

Robblee, et al., "Activated IR: An Electrode Suitable for Reversible Charge Injection in Saline Solution", *Journal Electrochemical Society*, vol. 130, pp. 731–733.

Rose, et al., "Assessment of Capacitor Electrodes for Intracortical Neural Stimulation", *Journal of Neuroscience Methods*, vol. 12, pp. 181–193 (1985).

Kazimierczuk, et al., "Exact Analysis of Class E Tuned Power Amplifier at any Q and Switch Duty Cycle", *IEEE Transactions on Circuits and Systems*, vol. CA-S-34:2, pp. 149–159 (Feb. 1987).

Heetderks, "RF Powering of Millimeter and Submillimeter-Sized Neural Prosthetic Implants", *IEEE Transactions and Biomedical Engineering*, vol. 35:5 (May 1988).

*Primary Examiner*—William E. Kamm
*Attorney, Agent, or Firm*—Fitch, Even, Tabin & Flannery

[57] ABSTRACT

An implantable microminiature stimulator and/or sensor (microdevice) is housed within a sealed housing that includes all the requisite electronic circuitry for inductively receiving power and control signals to sense of biopotential or other biomedical signals and/or to generate electrical stimulation pulse(s) between opposing electrodes. In a preferred embodiment, the housing of the microdevice is tubular, with opposing electrodes extending from each end. The electrodes are self-attaching electrodes that attach to a nerve or muscle without suturing. The electrodes are configured to helically curl around the desired nerve, thereby permitting the microdevice to stimulate the nerve or muscle, or sense signals associated with the nerve or muscle, using a minimal amount of energy. The electrodes and microdevice are sufficiently small to allow attachment to a single nerve, thereby preventing tethering of the nerve or muscle, and to allow their implantation within living tissue through small incisions or puncture holes. The muscle or nerve to which the microdevice is attached may be of any type, e.g., skeletal, smooth or cardiac.

22 Claims, 5 Drawing Sheets

IMPLANTABLE MICRODEVICE WITH SELF-ATTACHING ELECTRODES

This application is a continuation-in-part of application Ser. No. 08/025,994, filed Mar. 3, 1993; which is a continuation of Ser. No. 812,051, filed Dec. 12, 1991 now U.S. Pat. No. 5,193,540.

BACKGROUND OF THE INVENTION

The present invention relates to implantable medical devices, and more particularly to an implantable microminiature stimulator (or "microstimulator") or microminiature sensor (or "microsensor") adapted to securely attach to one or more muscle or nerve fibers (or muscles or nerves) and to electrically stimulate the muscle nerve at the point of attachment in a controlled manner, or to sense one or more specific parameters that originate at or near the point of attachment. More particularly, the invention relates to an implantable microstimulator and/or microsensor (hereafter referred to as a "microdevice" or "microdevices") that uses helical electrodes for sensing, stimulating, and/or anchoring.

Neurological disorders are often caused by neural impulses failing to reach their natural destination in otherwise functional body systems. Local nerves and muscles may function, but, for various reasons, injury, stroke, or other cause, the stimulating nerve signals do not reach their natural destination. For example, paraplegics and quadriplegics have intact nerves and muscles and only lack the brain to nerve link, which stimulates the muscles into action.

Prosthetic devices have been used for some time to provide electrical stimulation to excite muscles, nerves or other tissues. Such devices have ranged in size and complexity from large, bulky systems feeding electrical pulses by conductors passing through the skin, to small, implanted stimulators which are controlled through telemetry signals, such as are discussed in U.S. Pat. No. 4,524,774 (invented by Hildebrandt). Other devices have comprised a centrally-implanted stimulator package sending stimulation signals to a multitude of distant target sites using a network of implantable leads and electrodes. Unfortunately, when a lead and electrode are attached to a muscle or nerve from a centrally-implanted stimulator package, the muscle or nerve is, in effect, tethered by the lead, which may cause discomfort, irritation and damage to the patient as the muscle or nerve moves with a limb or body organ associated with the muscle or nerve. What is needed, therefore, is a way to stimulate a muscle or nerve without tethering the muscle or nerve.

Complications, including the possibility of infection, arise in the use of muscle, nerve or other stimulators which have conductors extending through the skin or which have nerve-stimulating electrodes that puncture or penetrate the epineurium. Further, in the use of implanted stimulators, difficulties arise in providing suitable, operable stimulators which are small in size and have the capability to receive and store sufficient energy and control information to satisfactorily operate them without direct connection. Hence, what is needed is an implantable stimulator that avoids the use of through-the-skin conductors, epineurium-penetrating electrodes, or other tissue-penetrating electrodes, and is small enough to facilitate easy implantation, yet has sufficient capacity to receive and store energy and control information so as to provide useful muscle or nerve stimulation.

Disadvantageously, the construction of a tiny microstimulator or microsensor (microdevice) presents problems of its own, which are not encountered in the construction of larger-sized biomedical appliances. An extremely small size involves problems and solutions of a different nature than are ordinarily encountered. The appropriate design of a suitable, small microdevice which can be easily implanted, such as by expulsion through the lumen of a needle, is difficult to achieve. Notwithstanding the small size and required shape, the microdevice structure must contain means for receiving and storing sufficient energy to provide the desired stimulating pulses or the desired sensing function, as well as electronic circuitry that provides control of the characteristics desired for the stimulating pulse or sensing signal.

Further, the electrodes used with a microdevice must also be carefully selected. Such electrodes must not complicate the implantation process, i.e., the electrodes too must be small and flexible, yet be of sufficient strength and length to be securely attached to the muscle or nerve they are to stimulate or from (or near) which a desired parameter is to be sensed.

The present invention advantageously addresses the above and other needs.

SUMMARY OF THE INVENTION

In accordance with one aspect of the invention, a source of electrical energy located outside the skin, modulated by desired control information, is used to selectively control and drive numerous, small stimulators, each attached to (or otherwise electrically coupled to) a particular nerve, muscle, or muscle or nerve fiber located within a specific location within a patient's body. Thus, for example, a desired, progressive muscular stimulation may be achieved through the successive or simultaneous stimulation of numerous stimulators, directed by a single source of information and energy outside the body.

In accordance with another aspect of the invention, an implantable microdevice, e.g., a microstimulator or microsensor, is housed within a small, sealed, housing. Such housing includes all the requisite electronic circuitry for sensing a specified parameter or generating electrical stimulation pulses that can be applied to a selected nerve or muscle, as well as circuitry for inductively receiving power and control signals from an external source. In a preferred embodiment, opposing electrodes extend from each end of the housing. The electrodes are configured for self attachment to a desired muscle or nerve, thereby permitting the microdevice to stimulate the muscle or nerve, and/or to sense a given parameter at or near the muscle or nerve. In some instances, e.g., when sensing certain parameters, the electrodes simply anchor the microdevice to a desired sensing location. Any type of electrode attachment scheme known in the art may be used to attach the electrode to the muscle or nerve, such as using helical, deep brain, chip, or cuff electrodes. The use of helical electrodes is preferred, because such electrode can be easily wrapped around the muscle or nerve, and the helical shape of the electrode, like a spring, firmly holds the electrode in contact with the muscle or nerve. Advantageously, the electrodes and microdevice(s) are sufficiently small to allow attachment to a single muscle or nerve, thereby preventing tethering of the muscle or nerve.

In accordance with a further aspect of the invention, a single microdevice includes circuitry for performing both the stimulating and sensing function.

In accordance with yet another aspect of the invention, the microdevice includes telemetry circuitry so as to provide telemetry functions as well as stimulating and/or sensing functions. Such telemetry function allows limited information, e.g., a signal sensed by the sensing function, to be telemetered to an external location. Such telemetered information may be used as diagnostic information, e.g., to signal whether a lead or electrode has broken, or as control information, e.g., to signal whether the amplitude of a stimulating pulse needs to be adjusted. In the case of telemetering control information, a feedback system can thus be established that includes the implanted microdevice and an external controller in order to control the operation of the implanted microdevice in a desired manner.

In accordance with an additional aspect of the invention, the microdevice is of a size and weight that allows its implantation through a very small incision in the patient's skin. In some embodiments, such incision may be as small as the puncture hole of a hypodermic needle, with the microdevice being implanted through the lumen of such needle. In other embodiments, the incision may be made in conventional manner, but is still of very small dimensions, e.g., having linear dimensions of no more than about 5 to 10 mm.

Thus, one embodiment of the invention may be characterized as an implantable microstimulator that includes: (1) a microstimulator module having electronic circuitry housed therein that inductively receives power signals from an external source and generates electrical stimulation pulses as a function of control signals, which control signals are also received from the external source; and (2) first and second opposing electrodes electrically connected to the electronic circuitry and extending from the microstimulator module, with the electrical stimulation pulses being electrically applied to the first and second electrodes. The first and second electrodes have distal ends configured for self attachment to a muscle or nerve, e.g., by curling about the muscle or nerve. Advantageously, the microstimulator module, including the first and second electrodes, are of a size, shape and weight so as to permit their implantation within living tissue through a very small incision, e.g., a puncture hole made by a needle, with the microstimulator being implanted through the lumen of such needle. Further, as required, the first and second electrodes may be attached to the same muscle or nerve, with the microstimulator module being supported therebetween, thereby providing a complete implantable microstimulator module that moves or "floats" with the muscle or nerve. Hence, tugging of the nerve from an electrode tethered to a larger, non-floating stimulator is avoided.

Additionally, another embodiment of the invention may be characterized as an implantable microdevice of a size capable of insertion through an incision having linear dimensions of no more than about five (5) to ten (10) mm. Such microdevice includes: (1) a hermetically-sealed housing which is inert to body fluids and tissue; (2) helically shaped, inert, metallic electrodes hermetically sealed to the housing; (3) electronic control circuitry encapsulated within the hermetically-sealed housing; (4) a coil for receiving an alternating magnetic field to provide operating power and control for the microstimulator; and (5) at least one capacitor encapsulated within the hermetically-sealed housing for storing energy received through the coil. The electronic control circuitry is configured so that the microdevice functions as either a microstimulator, a microsensor, or as both a microstimulator and microsensor. Telemetry capability may also be selectively included within the electronic circuitry encapsulated within the hermetically-sealed housing.

Yet a further embodiment of the invention may be viewed as an implantable microdevice, e.g., a microstimulator, adapted for implantation within a patient's body. Such microdevice includes: (1) a hermetically-sealed housing that is inert to body fluids and tissue, the housing being of a size no greater than approximately 2 mm in diameter and 10 mm in length and being of a shape capable of implantation through a lumen of a needle; (2) a first electrode comprising an electrically-conductive stem extending into the housing and hermetically sealed to the housing at or near one end thereof, the first electrode further including a first distal end adapted for self-attachment to a muscle or nerve fiber or a bundle of muscle or nerve fibers; (3) a second electrode comprising an electrically-conductive stem extending into the housing and hermetically sealed to the housing at or near the other end thereof, the second electrode including a second distal end adapted for self-attachment to a nerve or muscle fiber or a bundle of nerve or muscle fibers; (4) a ferrite core encapsulated within the housing would with a prescribed number of turns of a fine, electrically-conductive wire, forming a coil; (5) electronic circuitry encapsulated within the housing and disposed at or near one end of the ferrite core; and (6) means for electrically connecting the electronic circuitry electrically to the coil and the first and second electrodes. In operation, information and power are received by the coil, inside the body, from an alternating magnetic field modulated in accordance with information, where the alternating magnetic field is generated from a source and location outside the body. Depending on the type of electronic circuitry used within the housing, the microdevice senses information through the electrodes, stimulates nerves or muscles through the electrodes, or both senses and stimulates through the electrodes. Telemetry functions may also be included within the electronic circuitry.

Still an additional characterization of the invention is that of a method of stimulating muscles or nerves within living tissue, or sensing signals derived from or near selected muscles or nerves within living tissue. Such method includes the steps of: (a) fabricating a microdevice, the microdevice having electrical circuitry within a miniaturized housing, the electrical circuitry being adapted to receive power and control signals from a source external to the microstimulator and to: (i) generate electrical stimulation pulses controlled by the control signals, with the electrical stimulation pulses, when generated, being applied between first and second terminal connection points located within the housing, when the microdevice is used as a microstimulator, or (ii) sense a prescribed signal present at said first and second terminal connection points, when the microdevice is used as a microsensor, and telemeter the sensed signals to the external source; (b) connecting first and second electrodes to the first and second terminal connection points, respectively, each of the first and second electrodes having attachment means at or near a distal end thereof for self-attachment to a muscle or nerve; (c) hermetically sealing the housing so that the first and second electrodes extend therefrom, whereby everything within the housing is protected from body fluids and tissue; (d) implanting the housing with the electrodes extending therefrom within the living tissue; (e) attaching the distal ends of the electrodes to at least one muscle or nerve; and (f) controlling the microdevice with the control signals so as to provide a specified microstimulator or microsensor function.

It is thus a feature of the invention to provide an implantable microdevice that can attach to a muscle or nerve without tugging on or tethering the nerve.

It is another feature of the invention to provide such a microdevice that is implantable through a very small incision in the patient's skin, thereby minimizing the amount of surgery required to implant it.

It is a further feature of the invention to provide an implantable stimulator and/or sensor system, utilizing a plurality of microdevices, wherein each of the microdevices is independent of the other microdevices. Thus, should there be an infection, it will most likely not spread to other microdevices because there is no physical connection between them. Hence, in the event of an infection, a massive explant surgery should not be required.

It is yet another feature of the invention to provide a microdevice having helical electrode(s) that may be implanted by a surgeon having a fiber optic probe with saline flowing therethrough. The fiber optic probe allows the surgeon to view the nerve or muscle by looking through the fiber optic probe, when properly positioned, and to use a hollow needle, e.g., 10 gauge, with a stylet attached to the microdevice to screw or otherwise position the helical electrode(s) around the muscle or nerve, and therefore complete the implant procedure by leaving only a few puncture wounds in the patient.

It is still an additional feature of the invention to provide a microdevice having opposing helical electrodes extending from each end thereof, with each helical electrode having a proper spiral direction associated therewith so as to allow both electrodes to be readily implanted by a surgeon during the same implant procedure while causing minimal puncture wounds to the patient.

It is another feature of the invention to provide an implantable microdevice that has electrodes that are self-attaching, and that therefore do not require any sutures. Such self-attaching electrodes may be used to anchor the microdevice so that it can perform its desired stimulating and/or sensing function. In some applications, e.g., sensing magnetic fields, sensing body position, sensing body acceleration, sensing saturated oxygen, which functions can be performed without the need for external electrodes, and hence where it is not necessary for electrically active electrodes to touch live tissue, the helical "electrodes" (helical wires) are simply used as anchors to hold the microdevice in a desired implant location.

It is an additional feature of the invention to provide such a microdevice that can be used to stimulate or sense the same muscle or nerve bundle in two different locations, thereby sensing or stimulating more than one population of muscle or nerve fibers within the bundle, while maintaining no mechanical or electrical interaction between the two sensing or stimulation sites.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention relates to a microdevice that uses a self-attaching electrode to anchor or otherwise secure the microdevice in a desired implant location, e.g., to a desired nerve bundle or muscle tissue. The microdevice may comprise an electronic stimulating device that derives operating power from an externally applied alternating magnetic field; with the microdevice being controlled by control information that modulates such magnetic field. Alternatively, the microdevice may comprise an implantable microsensor that senses a desired biomedical parameter, e.g., voltage, body position, pressure, magnetic field, chemical parameters such as pH, oxygen, salinity, glucose concentration, or the like, converts such sensed parameter to an electrical signal (if not already an electrical signal), and telemeters such sensed signal to a location outside the body. Such microsensor likewise derives operating power from an externally applied alternating magnetic field; with the microsensor being controlled, as required, by control information that modulates such magnetic field. Further, the microdevice may comprise a device that provides both stimulating and sensing functions.

The design and operation of a microdevice is described in U.S. Pat. No. 5,193,539. The microdevice circuitry is hermetically sealed in a tiny tubular housing, as described in U.S. Pat. No. 5,193,540. The teachings of the '539 and '540 patents, while directed to a microstimulator, are also applicable to a microsensor. Both the '539 and '540 patents are incorporated herein by reference.

The microdevice of the present invention interfaces with a nerve bundle or "nerve" (note, for purposes of this application, a nerve bundle or "nerve" is made up of a plurality of nerve fibers), or with a muscle bundle or "muscle" (a muscle bundle or "muscle" is made up of a plurality of muscle fibers), by way of self-attaching electrodes. Preferably, two such self-attaching electrodes are used, one extending from each end of the microdevice's housing. Advantageously, by using self-attaching electrodes, suturing of the electrodes to the nerve is not required.

It is noted that any type of self-attaching electrode may be used with the microdevice in accordance with the present invention. Self-attaching electrodes are described, e.g., in U.S. Pat. Nos. 4,920,979 (helical electrodes); 4,934,368 (cuff electrodes); or 4,573,481 (helical electrode arrays). Additionally, sutured electrodes or electrode arrays affixed to substrates that are sutured may also be used, such as is shown in U.S. Pat. Nos. 4,026,300 (woven sheet material coupling) or 4,590,946 (electrodes helically wound and secured to a sutured substrate); although using a sutured electrode configuration defeats one of the advantages of using self-attaching electrodes—ease of implantation. The '979, '368, '481, '300 and '946 patents are all incorporated herein by reference.

Figure 1A:
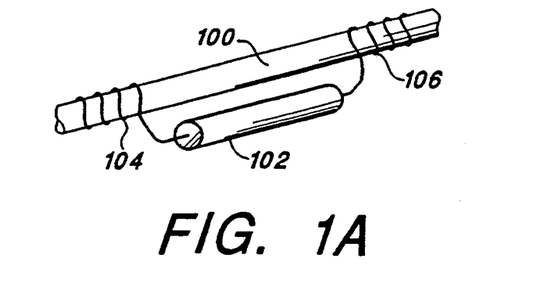
FIG. 1A schematically shows a microdevice attached to a muscle or nerve by two opposing helical electrodes.

The basic invention is illustrated in FIG. 1A, where there is shown a schematic representation of a microdevice 102 attached to a nerve 100 by two opposing helical electrodes 104 and 106. As described more fully below, the microdevice 102 is housed within a sealed housing, typically an elongated housing that has a generally tubular shape. One of the helical electrodes 104 extends from one end thereof and wraps around the nerve or muscle 100. (Hereafter, where reference is made to a "nerve", "nerve fiber" or "nerve bundle", it is to be understood that such reference is also intended to include reference to a "muscle", "muscle fiber" or "muscle bundle", as appropriate In other words, hereafter the term "nerve", including its various forms as a noun or adjective, is used as a shorthand notation for "nerve or muscle", including their various forms as a noun or adjective.) The other helical electrode 106 extends from the other end of the tubular housing and likewise wraps around the nerve 100. Preferably, the direction of the helical turns of the electrode 104 is opposite that of the helical turns of the electrode 106, which makes it easier to implant and attach the electrodes. Because the tubular housing is supported between the two helical electrodes 104 and 106, which electrodes firmly grasp onto the nerve 100 as their multiple turns wrap around the nerve, the microdevice 102 is effectively attached to the nerve, and "floats" with the nerve. That is, as the nerve moves, e.g., with the motion of a limb or body organ associated with the nerve, the microdevice also moves, thereby preventing the nerve from being tugged or tethered in any way by the electrode.

Figure 1B:
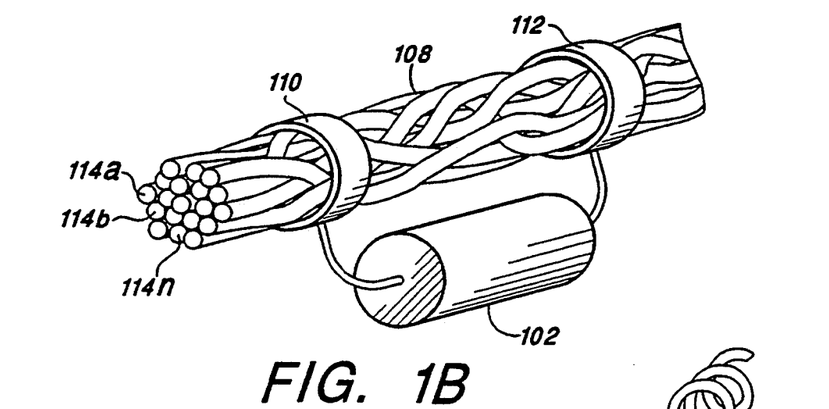
FIG. 1B schematically shows a microdevice attached to a muscle or nerve by two opposing cuff electrodes, and further illustrates the nerve being made up of a bundle of individual nerve fibers.

FIG. 1B schematically shows a microdevice 102 attached to a nerve 108 by two cuff electrodes 110 and 112, each being attached to respective ends of the housing of the microdevice 102. FIG. 1B also illustrates that the nerve 108 typically comprises a bundle of individual nerve fibers 114a, 114b, . . . 114n, which individual nerve fibers are twisted and intermingled along the length of the nerve bundle 108. Thus, the population of nerve fibers that make physical and/or electrical contact with the electrode 110 may not necessarily be the same population of nerve fibers that make physical and/or electrical contact with the electrode 112. Thus, by employing two spaced-apart electrodes as shown in FIG. 1B, whether such electrodes are cuff electrodes as shown in FIG. 1B, or helical electrodes as shown in FIG. 1A, or other equivalent electrodes, the electrodes are advantageously able to interface with different populations of nerve fibers. Hence, the same nerve bundle may be stimulated the same in two different locations in order to stimulate more than one population of nerve fibers within the bundle without any mechanical or electrical interaction between the two stimulation sites.

Figure 1C:
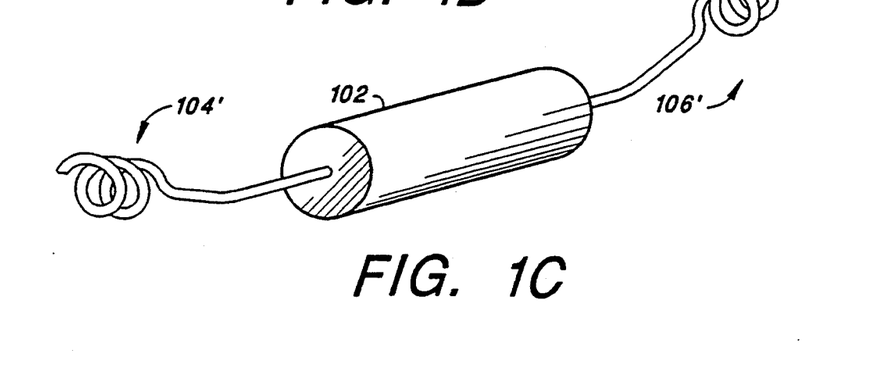
FIG. 1C depicts a microdevice having opposing helical electrodes where each helical electrode is configured to have only a few loose turns.
Figure 1D:
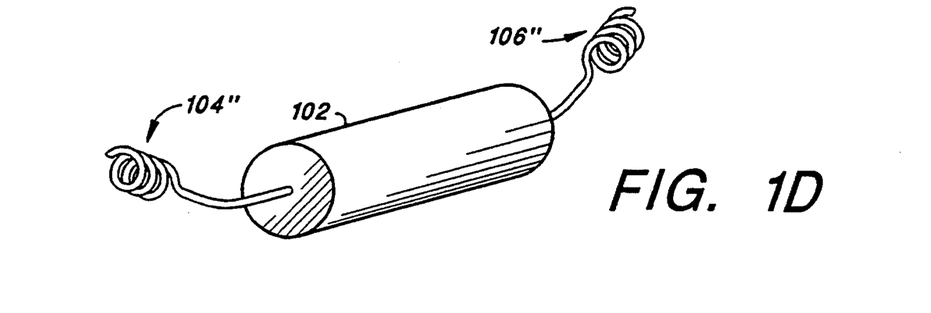
FIG. 1D depicts a microdevice as in FIG. 1C wherein each helical electrode is configured to have a multiplicity of tight turns.

FIG. 1C depicts the microdevice 102 having opposing helical electrodes 104' and 106' where each helical electrode is configured to have only a few loose turns. In contrast, FIG. 1D depicts the microdevice 102 having opposing helical electrodes 104' and 106', wherein each helical electrode 104' and 106' is configured to have a multiplicity of tight turns. Here, the terms "loose" and "tight" are relative terms, referring to the number of turns and/or the spacing between the turns. In general, a loose helical electrode is one having 1-2 turns, and a tight helical electrode is one having 3 or more turns. The type of helical electrode to be used depends upon the location of the implant and the size of the nerve. If the nerve is in a location where there is a significant amount of body motion, e.g., in a leg or arm, then a larger number of turns are desired to better hold the electrode in place around the nerve and prevent the microdevice from slipping. If the nerve is in a location where there is little motion, e.g., in the trunk of the patient's body, then a lesser number of turns are needed. In all situations, however, it is important that there be sufficient turns, or other attachment means, to assure good electrical and physical contact with the nerve.

Advantageously, the microdevice of the present invention may be implanted by making very small incisions or puncture holes in the patient's skin. Typically, the microdevice as described in the '539 and '540 patents, referenced above, has dimensions of the order of 10 mm long by 2 mm in diameter. Thus, an incision on the order of about 3 mm to 10 mm is all that is needed to longitudinally insert the microdevice under the skin. In some instances, as indicated in the referenced patents, the microdevice may even be implanted through the lumen of a needle.

Implantation of the microdevice may also be facilitated through the use of a fiber optic probe. A suitable saline solution flows through the fiber optic probe to keep its lens, as well as the area being observed, clear. The surgeon inserts the fiber optic probe under the skin, using conventional techniques, to locate a suitable implant site. Then, using a hollow needle, about 10 gauge, with a stylet attached to the microdevice, the microdevice is implanted at the implant location. The stylet is used to not only help maneuver the microdevice into the desired implant location, but also to help position the helical electrodes (or other self-attaching electrodes) around the nerve or muscle. In some instances, if needle electrodes are used (which also comprise a type of self-attaching electrodes), such needle electrodes may be pushed through the nerve or muscle using the stylet. Once the electrodes are in position, the needle and fiber optic probe can be removed, leaving the patient with as few puncture wounds following the procedure as possible.

When the above implant procedure is performed correctly, there is no need to puncture the epineurium, or equivalent protective tissue. (The epineurium is the outer sheath of connective tissue that encloses the bundles of fibers that made up a nerve.) Hence, the nerve is maintained protected within its natural sheath, without external penetration. Such protection minimizes the likelihood of infection at the nerve. Further, even if infection should occur, it will not likely spread to other attachment sites because there is no connection between the attachment sites. Thus, even in the event of an isolated infection, a massive explant of the microdevices should not be needed.

Advantageously, when two helical electrodes are used, one extending from each end of the microdevice as shown in FIGS. 1A, 1C or 1D, and where each electrode spirals in the proper direction (with one electrode spiraling in one direction, and the other electrode spiraling in the other direction), the above-described implant procedure may be used to position both electrodes with a minimal number of puncture wounds.

Further, it is noted that the helical electrode(s) can be positioned longitudinally and/or rotationally to optimize the stimulation or sensing points so as to activate the optimal family of neurons associated with the nerve, or so as to sense a desired signal, e.g., biopotential signal, associated with an optimal family of nerve fibers.

For some applications, e.g., where the microdevice is utilized as a microsensor and where one or more parameters are sensed that do not require the use of an electrode to perform the sensing function, such as is the case for sensing magnetic fields, body position, body acceleration, saturated oxygen, etc., the helical electrodes 104 and/or 106, or equivalent self-attaching electrodes shown in FIGS. 1A–1E, may simply comprise a helical wire(s) that is bonded to the housing of the microdevice and that is used to anchor the microdevice in a desired implant location relative to the nerve or muscle 100.

After implantation, it is best if the limb (or other body part) wherein the implant was placed can be immobilized for a few days. Such immobilization advantageously allows a fibrous capsule to form around the microdevice, which fibrous capsule locks the device in its implant position adjacent the nerve. Further, because the helix is a loosely open structure, the attachment of a helical electrode to a nerve does not constrict the nerve and its blood supply. Thus, the fibrous capsule that is formed locks the entire implant in place, with the nerve and blood supplies remaining in their natural, non-constricted, condition.

Figure 1E:
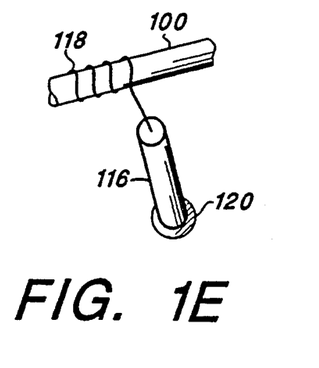
FIG. 1E shows a microdevice made in accordance with the invention that is attached to a nerve by a single helical electrode.

FIG. 1E shows a microdevice 116 made in accordance with the invention that is attached to a nerve 100 by a single helical electrode 118. In such instance, the return electrical path from the electrode 118 to the microdevice 116 is through the nerve 118 and body fluids to an indifferent electrode 120, typically located at the opposite end of the microdevice housing.

Figure 2:
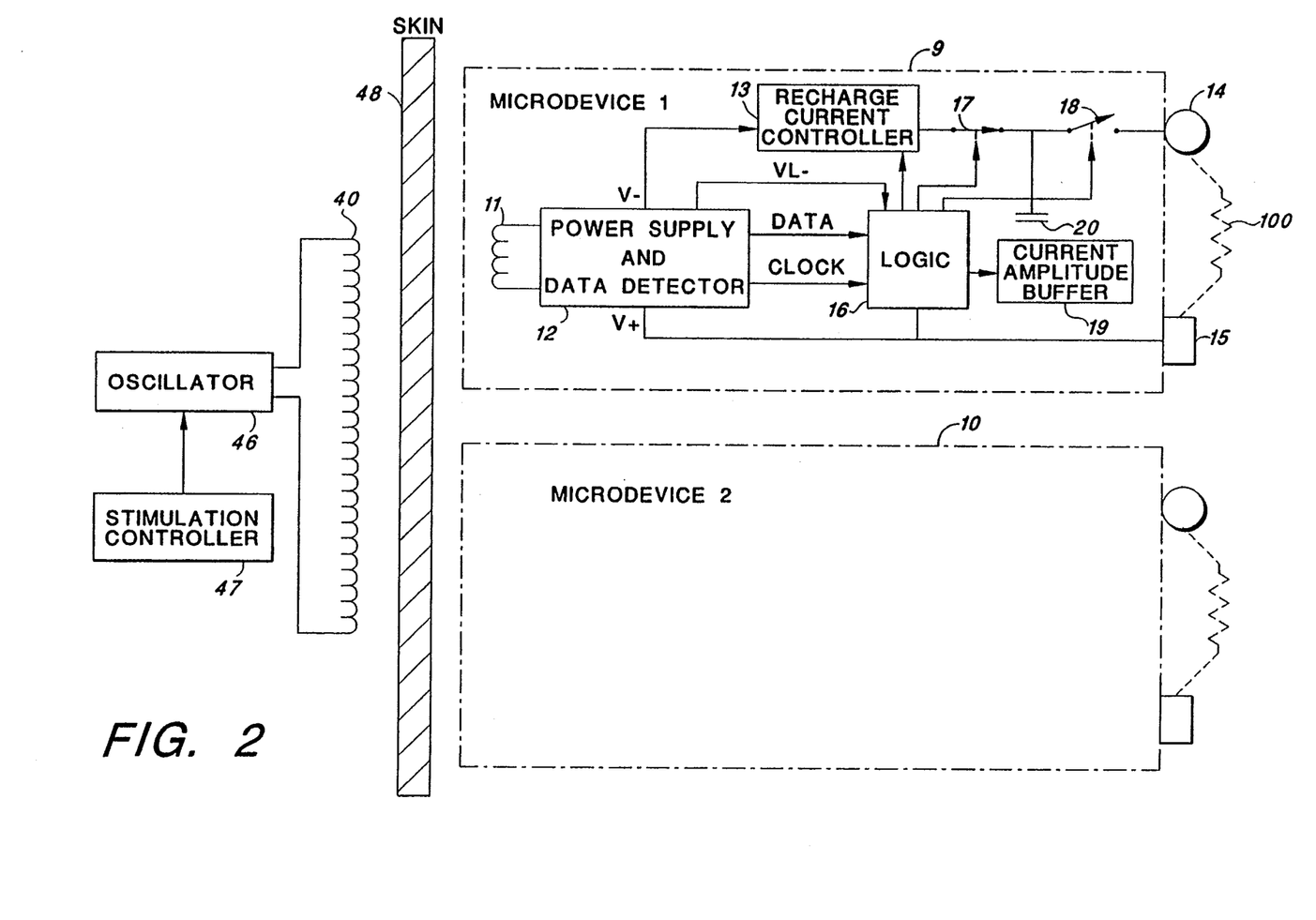
FIG. 2 is block diagram illustrating the transcutaneous transmission of power and information to implanted microdevices that perform a stimulating function.

Referring next to FIG. 2, there is shown a block diagram illustrating the transcutaneous transmission of power and information to one or more implanted microdevices that are used as microstimulators. In particular, as seen in FIG. 2, power and information are coupled to implanted microdevices 9 and 10 by an oscillator 46, driven by a stimulation controller 47. A coil 40 is driven by the modulated oscillator 46, which in turn is driven by the stimulation controller 47. Underneath (shown to the right of) skin 48 are implanted microdevices 9 and 10. (While only two such microdevices are shown, it is to be understood that any number of microdevices may be used.) Microdevice 9 is shown in greater detail. Secondary coil 11, within microdevice 9 receives energy and control information from the modulated, alternating magnetic field provided by coil 40 and passes such energy and information to power supply and data detector 12 which, in turn, provides power through an electrode recharge current controller 13 to stimulating electrodes 14 and 15. While electrodes 14 and 15 are drawn in FIG. 2 as being a "ball" and "rectangle", respectively, it is to be understood that such representation is only symbolic. For purposes of the present invention, at least one of the electrodes 14 or 15, and typically both electrodes, is a self-attaching electrode, as described above. That is, typically at least electrode 14 will be a helical electrode or cuff electrode (or other self-attaching electrode) that attaches to the nerve.

FIG. 2 shows secondary coil 11 at or near the surface of the skin 48. Such is for illustration only. The microdevice 9 or 10 may be much deeper, if desired, or at any location within the body of the patient, i.e., within an arm or leg. The transmitting coil 40 need not be directly aligned with the receiving coil 11, but the receiving coil 11 may be anywhere along the length of the transmitting coil 40, and even for some distance beyond the ends of the coil 40. In one experimental determination, it was found that the microdevices may lie as far as about 5 cm outside the volume encompassed by coil 40. The two coils 40 and 11 thus function like the windings of a transformer, with one coil being inductively coupled to the other.

The power supply portion of 12 provides the operating and stimulating voltages for the microdevice, with the energy being derived from the signal received through the coil 11 as coupled from the coil 40. The operating voltage may be at two levels, for example, approximately $-7$ to $-15$ volts, for providing stimulating pulse energy storage; and $-2$ to $-4$ volts for providing operating power for digital logic 16. Data detector 12 also provides clock and digital data information to logic 16 which decodes the control information contained within the modulated, alternating magnet field. Such decoded information is used by the logic 16 to control switch 17 which controls the charge stored on the capacitor 20, connected between electrodes 14 and 15. Capacitor 20 is located inside the hermetically sealed tube that comprises the housing of the microdevice 9. In some embodiments, the capacitor 20 may actually be found outside of the housing using the electrodes 14 and 15, but still between the electrodes 14 and 15, as described in the '539 and '540 patents cited above. Logic 16, which is preferably high speed, low current, silicon gate CMOS, also controls switch 18 (which may be a transistor switch), which switch 18 controls the stimulating pulse current (which is a discharge of the stored charge on the capacitor 20). The discharge current flows between electrodes 14 and 15 through the nerve 100 (represented in FIG. 2 by a resistor drawn with a dashed line). Logic 16 also controls current amplitude buffer 19. The buffer 19, which may be realized by an adjustable or programmable resistor, controls the amount of current allowed to flow in each stimulating pulse.

Figure 3:
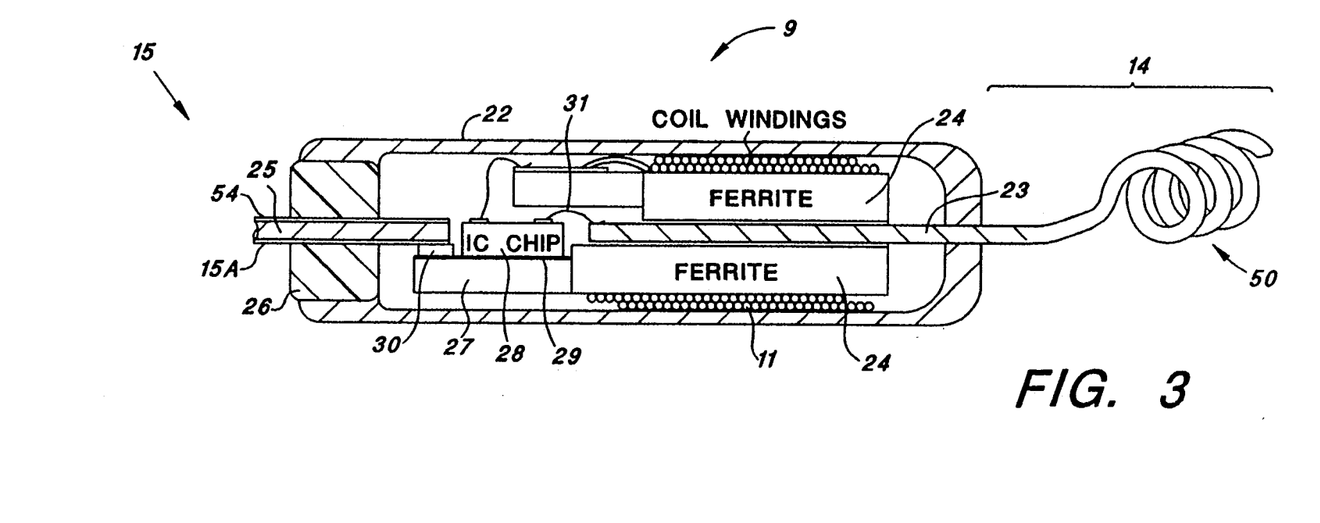
FIG. 3 is a cross-sectional side view of a microdevice.

Turning next to FIG. 3, it is seen that electrode 14 includes a distal tip portion 50, that may be wound in the shape of a helix (or otherwise attached to a self-attaching electrode), and a stem portion 23 that extends into the microdevice. In a preferred embodiment, the electrode 14, including the distal tip portion 50 and stem portion 23, is made from tantalum, platinum, iridium, or equivalent metal conductor that is compatible with body fluids. The electrode 14 is formed, e.g., from a wire that has been formed and processed so as to assume the desired helix shape at the tip portion 50.

As further seen in FIG. 3, electrode 15 is placed at the opposite end of the microdevice from electrode 14. Only a stem portion 25 of the electrode 15 is shown in FIG. 3, but it is to be understood that the electrode 15 may be formed and shaped in the same manner as the electrode 14 when two self-attaching electrodes are used. Electrode 15 may be made, e.g., from anodized, sintered tantalum, or other suitable metal that is compatible with body fluids. The stem portion 25 extends into the microdevice.

If only one self-attaching electrode is used (as seen in FIG. 1E), then the electrode 15 may include a pellet of tantalum (or other suitable metal) that is exposed outside the stimulator, connected to the stem portion 25. For example, in one configuration, when electrode 14 comprises the only self-attaching electrode, then electrode 15 may be constructed of powdered tantalum metal molded and sintered into a pellet on the end of a 0.25 mm diameter wire, tantalum stem. It is then anodized, to form a thin anodized layer 15A, and the tantalum stem is threaded through a glass bead of N51A soda-lime glass and the portion of the stem protruding inside the glass bead is gold plated (plating not shown). The anodization may be left until after the housing is sealed to the glass bead because the heat may affect the anodization. The glass bead is preferably of the size of the tantalum pellet, approximately 1.5 mm in diameter and 1 mm in width. The entire length of the tantalum electrode is approximately 2.8 mm. The porous nature of the pellet allows intimate relationship with the body fluids, but is of sufficiently small cellular structure that fibrous growth does not occur within the cells. The pellet is the outer, exposed portion of the electrode and is formed as a cylindrical section approximately less than 2 mm long and 2 mm in diameter (approximately 6 or 7 $mm^3$). The outer exposed pellet thus comprises, by its porous structure and anodized layer, an electrolytic capacitor, which may be used in lieu of the capacitor 20. The capacitance of such an external electrolytic capacitor, provided by a tantalum electrode 15 as described above, coupled with an iridium counter electrode 14, can be significant, being on the order of 2 to 30 microfarads. For greater capacitance, the outer cylindrical section of tantalum electrode 15 can be larger, but it is noted that sufficient capacitance can be achieved by a volume of only 7 $mm^3$. It has been found that anodized tantalum has a very low DC leakage level when biased up to 80% of the anodization voltage and tends to self-heal in body fluids.

As indicated above, when two self-attaching electrodes are utilized, as shown, e.g., in FIGS. 1A–1D, then a discrete capacitor 20 is placed within the microdevice. When the microdevice is used as a stimulator, the capacitor 20 is placed in series circuit with electrodes 14 and 15. (When the microdevice is used as a sensor, the capacitor 20 may be used in the power supply circuit 12 in order to store energy received through the coil 40 to provide operating power for the sensing circuits, and particularly the telemetry circuits, described below.) Such discrete capacitor, constructed in accordance with integrated circuit fabrication techniques known in the art, occupies a substantial amount of space within the microdevice.

Advantageously, all of the elements needed to receive and store modulated, electrical energy and to decode and use the modulating information to cause, e.g., stimulating pulses, or to sense biomedical parameters and telemeter signals representative of such parameters, are provided within the microdevice. All elements are housed within the housing of the microdevice except for the exposed electrodes.

Thus, a preferred embodiment is one in which one or both of the electrodes 14 and 15 are formed in the shape of a single or plural nerve cuffs, as taught in U.S. Pat. No. 4,934,368, or in the shape of helical electrodes, in order to attach to a desired nerve. Platinum wires, for example, extending out of each end of the microdevice may be connected to the appropriate nerve cuff. Alternatively, the distal ends of platinum wires, extending out from each end of the microdevice, may be formed in the shape of the helical electrodes. With the electrodes in direct contact with the nerve, the stimulating pulse does not need to be as large as it would if such direct contact did not exist. Hence, in the case of a microstimulator, the size of the storage capacitor 20 need not be large. Although the size is miniature, when nerve cuffs are used, as shown in FIG. 1B, the device will normally have to be surgically implanted, as opposed to implanted through the lumen of a needle. When helical electrodes are used, as shown in FIGS. 1A, 1C and 1D, the device may be surgically implanted, or implanted through the lumen of a needle, as described above. Indeed, that is one of the advantages of using helical electrodes—plantation of the device is achievable with minimal punctures or incisions in the patient.

As seen in FIG. 3, which shows a cross-sectional side view of the microdevice 9, a housing 22 encloses the microdevice. In a preferred embodiment, the housing 22 comprises glass capillary tubing approximately 10 mm long and having an outer diameter of approximately 2 mm. Such glass capillary tubing is preferably a biocompatible, lime glass or borosilicate glass and is commonly available from or through glass fabrication houses such as Kimbel Glass or Corning Glass.

Alternatively, the housing may be a ceramic, cast or molded epoxy or silicon rubber, or other material which is hermetically-sealable, inert and suitable for implantation.

At one end, the glass tube is hermetically-sealed to the electrode 14, which electrode comprises an iridium, tantalum, or platinum wire, including the stem 23 that extends into the microdevice 9. A wire of, e.g., 0.15 mm to 0.25 mm be used, with one end cold-formed to provide a flat for bonding a wire thereto, to make electrical connection to the IC chip 28 within the microdevice.

It is important to select a glass for the housing 22 which is stable in body fluids and which matches pretty well the coefficient of thermal expansion of the material from which the electrodes are made, e.g., tantalum, iridium or platinum, because of the heating operations involved in fusing the electrodes to the glass housing. Glass capillary tubing, N51A, has a coefficient of thermal expansion similar to tantalum and iridium and thus may be sealed thereto. The tubing is cut off square about 2 mm beyond the end of the ferrite core 24.

In operation of the microdevice as a microstimulator, the storage capacitor 20 is charged to a suitable stimulating voltage. Upon discharge, or partial discharge of the charge, as controlled by the closing of the switch 18 and by the setting of the current amplitude limiter 19 (FIG. 2), an electrical current pulse flows between the two electrodes 14 and 15, thereby stimulating the nerve 100.

At the other end of the microdevice from electrode 14 is the electrode 15. Such electrode 15 also has a stem 25 extending into the microdevice. The stem 25 and electrode 15 are preferably made from the same wire, e.g., iridium, tantalum or platinum wire. In some instances, e.g., as indicated in the '540 patent cited above, it may be desirable to anodize the stem 25 with an anodized layer 15A. The process for such anodizing is described in the '540 patent.

There are various methods of assembly associated with the microdevice 9. In the preferred method, the entire internal assembly is put together and inserted into the housing from one end of the housing or the other. Prior to inserting the assembly, a glass bead 26 is threaded onto the stem 25 and fused thereto. The inner end of the stem is gold-plated. A metallized film 29 is deposited on the bottom ferrite shelf. The IC electronics chip 28 is adhered to the metallic film 29 on ferrite shelf 27 by silver epoxy, silver solder, an indium-based solder, or other suitable conductive adhesive. Two metallized pads 32 and 33 are created on the top half of the ferrite core. A polyamide, solder resist line, or barrier 38, is added. The tantalum stem 25 is resistance welded or soldered to the weld shim 30.

An alternate method of connection of the stem 25 to electronic chip 28, rather than by means of metallized film 29 and the substrate of the electronic chip 28, is to replace the shim 30 and the metallized film 29 with a small metallized pad disposed on the ferrite shelf 27 to which both stem 25 and electronic chip 28 are connected by flying wire bonds, or other means.

The stem 23 of electrode 14 is inserted through the ferrite channel of the bottom half of the ferrite core and is connected electrically to the electronic chip 28 by electrical conductor 31. A silver epoxy may be used to reinforce such electrical connection. Additional silver epoxy may be used to fill up the channel and provide a heat sink for the electrode 14.

Figure 4:
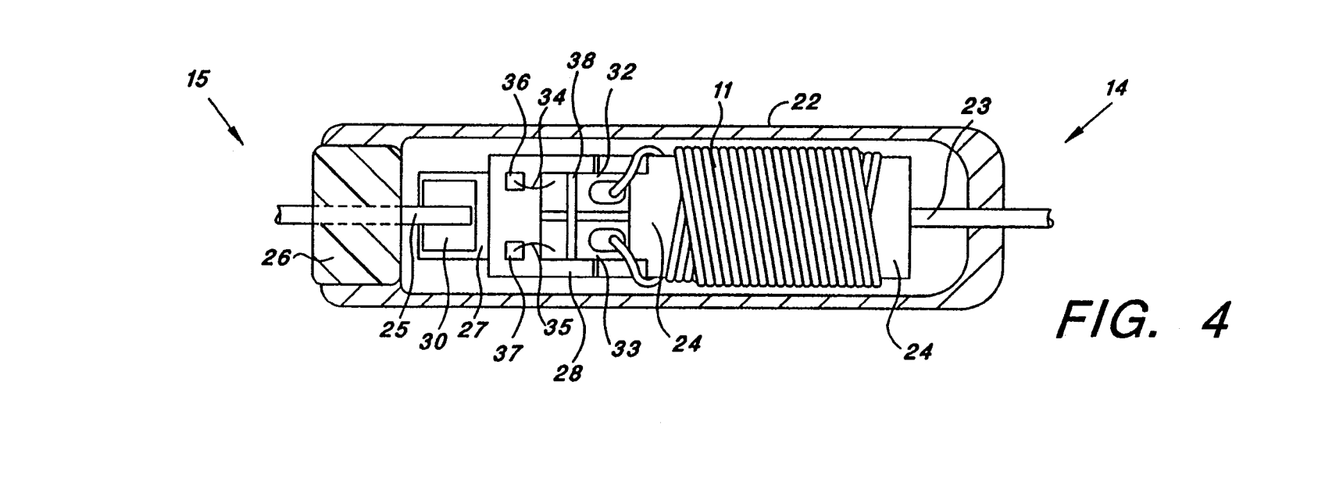
FIG. 4 is a top view of a microdevice with the housing in cross-section.

The top half of the ferrite core is placed over the bottom half of the ferrite core and one end of the coil wire is soldered to a metallized pad, 32, for example, and the coil is wound on the ferrite and the other end is soldered to the other metallized pad 33. Gold wires are bonded between the metallized pads 32 and 33 and the electronic chip pads 36 and 37. A junction coat is applied.

The electrode 14, including its stem 23, along with the entire inner assembly, are then inserted into one end of the glass capillary tube 22. The glass is sealed to the smooth surface of the stem 23, by bringing the glass and stem into an oxy-acetylene flame and rotating them within the flame. The sealing operation may be viewed under a microscope. It will be noted that the glass will shrink backward during melting.

The glass bead 26 on the stem 25 of electrode 15 on the other end of the microdevice is flame-sealed, or fused, to the glass tubing, housing 22.

The outwardly exposed portions of the electrode 15 may then be anodized, as explained previously, if necessary to provide additional external storage capacitance.

The metallized pads 32 and 33 on the top half of the ferrite core 24 may be made of indium solder and no barrier 38 is then required. Metallized pads 32 and 33 may be created of palladium, silver, indium, or solder, or mixtures thereof. The flying, gold bond wires may be attached directly from such pads to the electronic chip 28.

Other means may also be used to make the electrical connections within the microdevice. For example, a polyamide cap (Kapton) may be used. It is placed on the electronic chip 28 and provides solder pads on the top for connecting to the electrodes and the coil and on the bottom for connecting to the electronics chip 29. Thruhole connections, in the cap itself, make connections between the top and bottom of the cap.

Testing for hermeticity may be done by helium, but the helium may leak out before the test can be made. Finished devices are best tested by soaking in a dye solution and rejecting those parts that exhibit streams of bubbles or internal dye droplets.

The microdevice shown in FIGS. 3 and 4 illustrates the coil 11 which, depending on the particular application, has approximately 200 turns or more, to provide the necessary induction for the coupling of the magnetic flux associated with the alternating magnetic field. (Where telemetry is also provided within the microdevice, an additional coil is also provided, as indicated below.) In one preferred embodiment, approximately 250 turns of 51 AWG, (0.00102" diameter or smaller) insulated, copper wire is wound in two layers on the ferrite core 24, having a diameter of approximately 0.050". Such construction will by its own distributed capacitance be resonant at approximately 2 MHz. Although an air core and other cores of high-permeability and low losses could be made to work, a ferrite core is preferred. A particular core material which was used and found satisfactory was a low conductivity, high permeability, nickel-zinc ferrite stock, having a permeability of 800. It was formed by cutting and grinding two half cylinders, to the shape shown in FIGS. 3 and 4, with a groove in each, to form a hollow core when the two half cylinders were placed together.

The bottom half of ferrite core 24 is longer than the top half and provides a shelf 27 on which to mount the electronic chip 28 (a custom, integrated, microcircuit chip) for the microdevice. It is noted that the top half of ferrite core 24 extends over electronic chip 28 and on the top surface of ferrite core 24 are disposed the metallic pads 32 and 33, FIG. 4 to which are connected the ends of the coil. In a preferred embodiment, electronic chip 28 is a double-poly P-well CMOS (3 micron) process so that the substrate is at the V+ supply rail to which the tantalum stem of electrode 15 is connected. It is noted that both ends of the coil 11 are electrically connected to provide input to the electronic chip 28, providing the energy (for powering the microdevice) and the modulation (control) information to such electronic chip 28.

One output of electronic chip 28 is to the electrode 15, and is shown in FIG. 3 as being through the substrate (base) of the electronic chip 28 to a thick, conductive film 29 which may be plated or adhered to ferrite shelf. Electrical connection between the electronic chip 28 and the film 29 may be accomplished by a silver-filled conductive epoxy or other electrically conductive means. The preferred thick, conductive film is screenable or imageable (by screen printing or photolithography or other imaging method). An alloy of the platinum group and gold (specifically, Pt/Pd/Au) in a fritted paste is preferred. Such is then fired for about 60 minutes, being raised evenly, 50 degrees Centigrade per minute, to approximately 850 to 1050 degrees centigrade in 30 minutes and cooling at the same rate. Such film shows good weldability and good solderability.

Weld shim 30, which is conductive, is also bonded or otherwise adhered to conductive film 29 and is resistance welded, or otherwise electrically connected to tantalum stem 25. Stem 25 comprises part of electrode 15 and extends through glass bead 26 to the exposed pellet of tantalum electrode 15.

Electrical connection between the stem 25 and the electronic chip 28 may also be made by a wire-bond between them or by a flying wire bond from each of them to a small metal pad (not shown) on ferrite shelf 24. Such connection may also be made as described in connection with FIG. 5, hereafter.

The other output of electronic chip 28 is connected to stem 23 by means of wire 31.

FIG. 4 is a top view of the microdevice 9 with the housing shown in cross-section. The ends of coil 11 are connected to two metallized pads 32 and 33 (of palladium-silver, for example) plated on ferrite 24, by means of conductive epoxy or soldering. Such pads 32 and 33 are connected by flying, gold wires 34 and 35 which are bonded to aluminized pads 36 and 37 on electronic chip 28 and protected with a junction coat. Barrier 38, which may, for example, be polyamide isolates the conductive epoxy and solder from flowing to undesired areas.

The microdevice 9 may be filled with a harmless, inert gas which is also compatible with the internal structure of the microdevice. Prior to fusing of the second electrode to the housing, the inert gas may be introduced into the microdevice, or the microdevice may be assembled in an inert gas atmosphere. The inert gas may be 10% helium and 90% argon or krypton or other commonly-used, suitable, biologically-compatible gas. Assembly in a dry, relatively clean atmosphere has been found suitable. All epoxy inside the microdevice must be allowed to fully cure before sealing, otherwise undesired by-products are generated within the microdevice as the epoxy cures.

Figure 5:
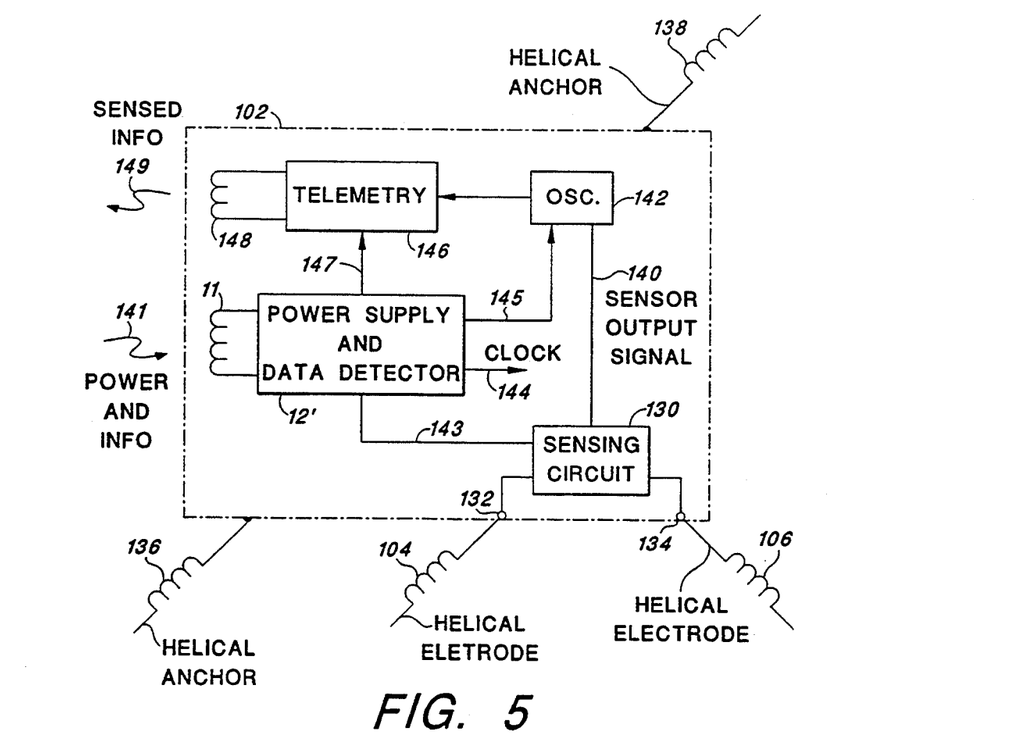
FIG. 5 is a block diagram of a microdevice that includes circuitry for sensing a desired parameter and telemetering a signal to an external source representative of the sensed parameter.

Referring next to FIG. 5, a block diagram of a microdevice 102 is shown that includes circuitry for sensing a desired parameter, e.g., a biomedical parameter, and telemetering a signal representative of the sensed parameter to an external source or location. The microdevice 102 includes a power supply and data detector 12' that receives power signals and information through a coil as described above in connection with FIGS. 2–4. Also included within the device 102 is a sensing circuit 130. The sensing circuit 130 may comprise any type of sensor circuit known in the art, or yet to be developed, such as a circuit to sense voltage; body position; pressure; magnetic field from a nearby magnet (to obtain an angle); chemical parameters, such as pH, oxygen, salinity, glucose concentration, or the like. For sensing some parameters, such a biopotential voltages, the sensor circuit 130 is connected to a pair of terminals 132 and 134, and the helical electrodes 104 and 106 are connected to such terminals. In such instances, the parameter that is sensed is thus sensed through the electrodes 104 and/or 106.

For sensing other parameters, such as body movement, acceleration, or certain chemical parameters, the electrodes 104 and 106 may not be needed to sense the desired biomedical parameter. In such instances, the desired parameter is either sensed through circuitry or elements included within the sensing circuitry 130, as is the case for sensing body movement or acceleration, see, e.g., U.S. Pat. Nos. 4,940,052 or 5,010,893; or is sensed through another type of parameter interface, e.g., an optical interface used to measure oxygen saturation based on reflected spectral components of incident light, see, e.g., U.S. Pat. No. 4,815,469. The '052, '893 and '469 patents are incorporated herein by reference. Where the electrodes 104 and 106 are not needed to sense the desired parameter, they still may be used solely for anchoring purposes. Further, instead of or in addition to the electrodes 104 and 106, which electrodes 104 and/or 106 are electrically connected to the sensing circuitry 130 through the terminals 132 and 134, anchoring "electrodes" 136 and/or 138 (which are not electrodes in the classical sense, but are simply wires formed in the shape of a helix) may be bonded to the housing of the microdevice 102 at one end and be utilized to help anchor the microdevice 102 into a desired implant position.

Still referring to FIG. 5, the sensing circuit 130 generates a sensor output signal, appearing on signal line 140, representative of the parameter that is sensed. (Note a signal appearing on a referenced signal line may also be referred to by the same reference numeral as is used for the signal line, e.g., the "sensor output signal 130.") This sensor output signal is directed to an oscillator circuit 142, or equivalent, where it modulates an oscillator signal. Alternatively, a clock signal 144, obtained from the power supply and data detector circuit 12' may be used as an oscillator signal (or may be used to derive an oscillator signal) that is modulated by the sensor output signal 140. In either event, the modulated oscillator or clock signal is directed to a telemetry circuit 146. The telemetry circuit 146, is coupled to a coil 148. The coil 148 receives the output of the telemetry circuit 146 and transmits it through the coil 148 so that it can be received by an external receiving circuit (not shown in FIG. 5). Thus, in this manner the external receiving circuit is able to monitor various parameters sensed by the sensing circuit 130. Note that information signals received by the power supply and data detector circuit 12' are used as control signals 143, 145 and 147 to control the operation of the sensing circuit 130, the oscillator 142 and telemetry circuit 146 in accordance with a specified mode of operation.

Thus, in operation, the microdevice 102 shown in FIG. 5 receives power and control signals 141 from an external source, senses a specified parameter or parameters through sensing circuit 130, and returns a sensed information signal 149 to the external source. In this manner, the external source may, in effect, function as a recording device that records, or otherwise stores, various parameters that are sensed at the specific sensing locations that are at or near the electrodes 104 or 106, or otherwise near the implant location of the microdevice 102.

Figure 6:
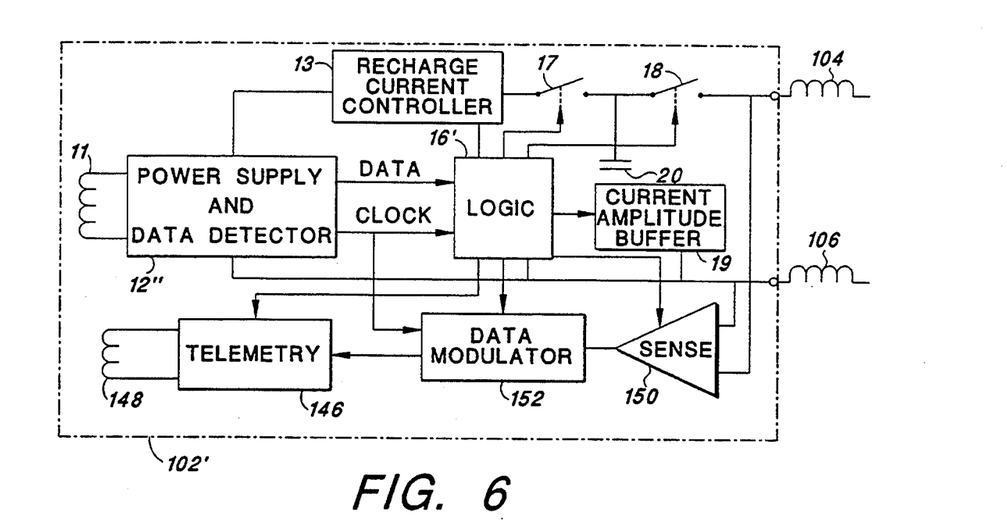
FIG. 6 is a block diagram of a microdevice that includes both sensing and stimulating circuitry.

Turning next to FIG. 6, a block diagram is shown of a microdevice 102' that includes both sensing and stimulating circuitry. Hence, the microdevice 102' is able to stimulate a nerve or muscle, as well as sense a specified biomedical parameter. The power supply and data detector 12" included in the microdevice 102' is substantially as described previously in connection with FIGS. 3 and 4. The stimulating function is provided by logic circuit 16' current charge regulator 13, current discharge regulator 19, capacitor 20, and switches 17 and 18, as described above. The current stimulation is provided between helical electrodes 104 and 106.

The sensing function provided by the microdevice 102' is aimed at sensing a biopotential signal associated with a contracting muscle, or a neural impulse associated with a nerve, and such signals are sensed through the same electrodes 104 and 106 as are used for stimulation. A sense amplifier 150 amplifies and filters the signals sensed through the electrodes 106 and 108. The amplified and filtered signal is then sent to a data modulator 152, where the signal modulates a clock signal obtained from the power supply and data detector circuit 12". The modulated clock signal is then sent to a telemetry circuit 146. The telemetry circuit 146 transmits the signal through the antenna coil 148. Transmission is preferably accomplished via a radio frequency (RF) carrier signal having an appropriate carrier frequency. Inductive coupling may also be used in some embodiments, the same as is used to couple power and information into the circuit 102'.

Control signals obtained from the logic circuit 16' control the operation of the sense amplifier 150, the data modulator 152 and the telemetry circuit 146. For most applications, operation of the telemetry and sensing circuits is done on a sampled basis, with a telemetry pulse being generated at a specified rate, e.g., 0.5–10 pulses per second. When not used, the sense amplifier 150, data modulator 152 and telemetry circuit 146 may be turned OFF.

Figure 7:
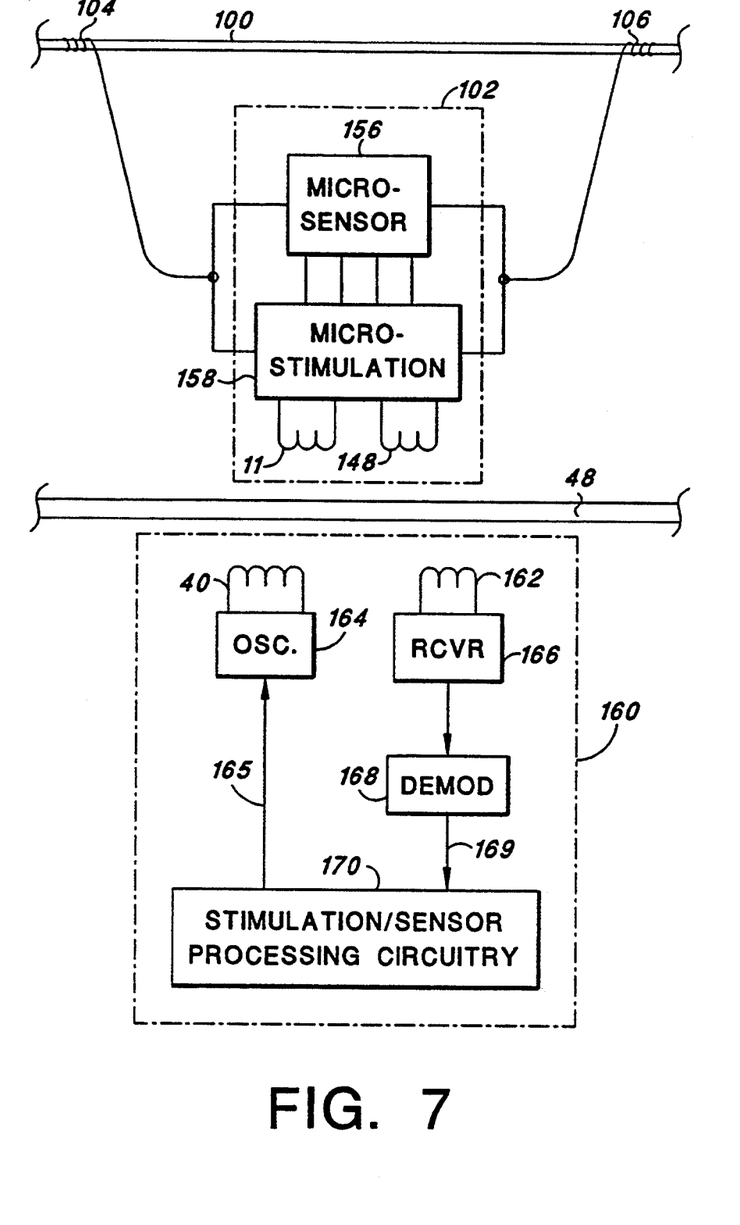
FIG. 7 is a block diagram of an implantable microdevice and an external controller, and illustrates the concept of using feedback information sensed by the microsensor portion of the microdevice, telemetered to the external controller, to control the microstimulator portion of the microdevice.

Referring next to FIG. 7, a block diagram of an implantable microdevice 102, having a sensing portion 156 (or microsensor 156) and a stimulator portion 158 (or microstimulator 158), and an external controller 160 is shown. FIG. 7 thus illustrates the concept of using feedback information sensed by the microsensor portion 156 of the microdevice 102, telemetered to the external controller 160, to control the microstimulator portion 158 of the microdevice 102. As shown in FIG. 7, the external controller 160 includes an oscillator 164 for driving the coil 40 with a power signal that is modulated with control information. The oscillator 164 is modulated by a control signal that is generated by stimulation/sensor processing circuitry 170. Such circuitry 170 may take various forms, but is preferably realized using a processor circuit that may be readily programmed to operate in a desired mode of operation.

On the receiving side, the controller 160 includes a receiving coil 162 coupled to a receiving circuit 166. The signal received by the receiving circuit is demodulated by a demodulator circuit 168, with a resultant data signal 169 being directed to the processing circuitry 170. Based on the contents of the data signal 169, the type of information sent to the microdevice 102 via the coil 40 may be adjusted in a desired fashion.

For example, assume that the microdevice 102 is one of a plurality of such devices that are implanted in a patient's arm to selectively stimulate an arm muscle or nerve 100. Assume further that the microsensor portion 156 of the microdevice 102 senses motion of the arm and/or voltage signals or neuron impulses indicative of the depolarization and/or movement of the arm muscle tissue. Thus, the feedback provided by the microsensor portion 156, received through antenna coil 162, and manifest in the data signal 169 generated at the controller 160, provides confirmation as to whether a given stimulation pulse, or sequence of stimulation pulses, generated by the microstimulator portion 158 of the microdevice 102, has achieved a desired objective of moving the patient's arm a desired increment. If so, then the sequence of stimulation can move to an adjacent microdevice. If not, then the magnitude, or some other parameter, associated with the microstimulator 158, can be adjusted, e.g., increased in amplitude and/or width, in order to achieve the desired stimulation, and hence movement of the arm. In this manner, then, movement of the arm can be selectively controlled, using the body's own muscle tissue to effectuate the movement, but controlling the movement in a desired manner by virtue of the stimulation pulses that are generated and the feedback signals that are sensed.

Alternatively, control signals can be generated by the controller 160 to activate the microsensor 156 of the microdevice 102 so as to cause the microsensor 156 to sense the impedance between of the electrodes 104 and 106. (Such impedance can be readily checked by monitoring the amount of current that flows between the electrodes when a stimulation pulse of a given voltage amplitude is applied between the electrode terminals.) The impedance measurement thus made is then telemetered back to the controller 160, where the processing circuitry can readily determine if such impedance is within an acceptable range. If not, then that is an indication that either one of the electrodes has broken (impedance very high), or that there is an electrical short (impedance very low). In either event, an out-of-range impedance is an indication of a malfunction, and appropriate corrective action can be taken.

In some applications of the invention, more than one electrode pair may be used with the same microdevice. In such instances, a first pair of electrodes are used for stimulation, and a second and subsequent pair(s) of electrodes are used for sensing. Where multiple (more than two) sensing electrodes are used, sensing can be performed, as needed, between any selected combinations of the electrodes, as controlled by the control signals received from the external controller.

It is noted that rather than using a single microdevice 102' (as shown in FIG. 6) that provides both sensing and stimulating functions, some embodiments of the invention contemplate using a desired combination of inexpensive, microstimulators and microsensors, controlled by the same external controller. Thus, for example, a multiplicity of microstimulators may be implanted to stimulate a nerve or muscle for a desired purpose, and only one or two microsensors need be implanted, to sense whether the desired purpose is achieved.

It is noted that a microsensor device made in accordance with the present invention as shown in FIG. 5, or a combination microsensor/microstimulator device as shown in FIG. 6, may be fabricated in a tiny microdevice package using the same techniques as described above relative to the microstimulator device shown in FIGS. 2–4.

Advantageously, the integrated stimulator/electrode structure described above eliminates the failure mode associated with leaded helical electrodes. That is, tethered electrodes can be pulled from their implanted position by forces applied by the tether when joint or other motions occur. Therefore, since no tether is present in the microdevice/electrode design described herein, this failure mode is eliminated.

Further, as seen above, the microdevice with helical electrodes comprises a complete unit. Thus, when implanted, there is no stress on the electrodes or the housing (e.g., glass) of the microdevice. Rather, the microdevice becomes, as it were, an integral part of the nerve to which it is attached, without any external tethering or pulling on the nerve.

While the invention herein disclosed has been described by means of specific embodiments and applications thereof, numerous modifications and variations could be made thereto by those skilled in the art without departing from the scope of the invention set forth in the claims.

What is claimed is:

1. An implantable microstimulator comprising:
an hermetically sealed case wherein electronic stimulation circuitry is housed, said electronic stimulation circuitry including means for inductively receiving power signals and control signals from an external source and means for generating electrical stimulation pulses as a function of said control signals; and
first and second opposing electrodes electrically connected to said electronic stimulation circuitry and extending from said sealed case, said electrical stimulation pulses being electrically applied to said first and second electrodes;
said first and second electrodes having means at distal ends thereof for self-attachment to a nerve;
said microstimulator being adapted for implantation within living tissue with the means for self-attachment of the first and second electrodes being connectable to the same nerve, with said microstimulator interposed therebetween, the microstimulator attached to the nerve thereby floating with the nerve;
whereby tugging or tethering of the nerve is avoided.

2. The implantable microstimulator as set forth in claim 1 wherein said hermetically sealed case is tubular in shape, with said first electrode extending from one end thereof, and with said second electrode extending from the other end thereof.

3. The implantable microstimulator as set forth in claim 1 wherein said hermetically sealed case has a length that is no greater than about 10 mm.

4. The implantable microstimulator as set forth in claim 1 wherein said hermetically sealed case is made from a glass tube having a diameter no greater than about 2 mm.

5. The implantable microstimulator as set forth in claim 1 wherein said means for self-attachment at the distal end of said first and second electrodes comprises a resilient flexible material formed in the shape of a helix adapted to wrap around said nerve.

6. The implantable microstimulator as set forth in claim 5 wherein said flexible material at the distal end of said first and second electrodes comprises an inert metal belonging to a group of biocompatible metals that consists of titanium, iridium and platinum.

7. An implantable microdevice including:
a hermetically-sealed housing having a length of no more than about 10 mm which is inert to body fluids and tissue;
an electronic circuit substantially encapsulated within said hermetically-sealed housing, said electronic circuit including means for generating a stimulation pulse and means for sensing bioelectrical signals;
helically shaped, inert, metallic electrodes hermetically sealed to said housing at or near opposing ends thereof;
a coil within said housing for receiving an alternating magnetic field that provides operating power and control signals for said microdevice;
a capacitor encapsulated within said hermetically-sealed housing for storing power received through said coil;
said electronic circuit including means responsive to said control signals for operating said microdevice as a microstimulator in response to a first control signal, a microsensor in response to a second control signal, and as both a microstimulator and microsensor in response to a third control signal.

8. The microdevice as set forth in claim 7 further including monitoring means within said housing for monitoring the operation of said microdevice and telemetry means within said housing for telemetering a signal representative of said monitored operation to a non-implanted location external to said microdevice.

9. The microdevice as set forth in claim 7 wherein said housing is made from a material belonging to a group consisting of: glass capillary tubing, ceramic, epoxy and silicon rubber.

10. An implantable microdevice comprising:
a hermetically-sealed housing that is inert to body fluids and tissue, said housing being of a size no greater than 2 mm in diameter and 10 mm in length;
a first electrode comprising an electrically-conductive stem extending into said housing and hermetically sealed to said housing at or near one end thereof, said first electrode further including a first distal end configured for self attachment to a muscle or nerve fiber or a bundle of muscle or nerve fibers;
a second electrode comprising an electrically-conductive stem extending into said housing and hermetically sealed to said housing at or near the other end thereof, said second electrode including a second distal end configured for self attachment to a muscle or nerve fiber or a bundle of muscle or nerve fibers;
a ferrite core encapsulated within said housing having a plurality of turns of a fine, electrically-conductive wire wound therearound, forming a coil;
an electronic circuit encapsulated within said housing and disposed at or near one end of said ferrite core; and
means for electrically connecting said electronic circuit to said coil and said first and second electrodes;
said coil being positioned within said housing to receive an alternating magnetic field, modulated in accordance with information, and
said electronic circuit including means for controlling the microdevice to sense information through the electrodes, to stimulate muscles or nerves through the electrodes, or to both sense and stimulate through the electrodes, as controlled by the information that modulates the alternating magnetic field received by said coil.

11. The implantable microdevice as set forth in claim 10 wherein said first and second distal ends of said first and second electrodes each comprise a helical electrode that is wrapped around said nerve fiber or bundle of nerve fibers, whereby said microdevice attaches to said nerve fiber or bundle of nerve fibers without suturing.

12. The implantable microdevice as set forth in claim 11 wherein at least one of said first or second electrodes, said core, and said coil are radially smaller than, and can pass through, said housing to facilitate assembly of said microdevice.

13. The implantable microdevice as set forth in claim 10 wherein the first and second distal ends of at least one of said first and second electrodes includes a cuff electrode.

14. A method of stimulating a fiber within living tissue using a microdevice, said microdevice having electrical circuitry within a miniaturized hermetically sealed tubular housing, said electrical circuitry being adapted to receive power and control signals from a source external to said microdevice and generate electrical stimulation pulses controlled by said control signals, said electrical stimulation pulses, when generated, being applied between first and second electrodes, each of said first and second electrodes extending from opposite ends of said tubular housing and having attachment means at or near a distal end thereof for securing said electrodes to a fiber within living tissue, said method comprising:
(a) implanting said tubular housing with the electrodes extending from opposite ends thereof within said living tissue;
(b) attaching the distal ends of said electrodes to the fiber within the living tissue; and
(c) controlling said microdevice with said control signals so as to provide electrical stimulation pulses that are applied to the fiber through said electrodes.

15. The stimulation method of claim 14 wherein the attachment means of at least one of said first and second electrodes includes a distal end configured in a helical shape, and wherein the step of attaching the distal end of said at least one electrode to a fiber includes wrapping said helically shaped electrode around said fiber.

16. The stimulation method of claim 15 wherein the attachment means of both said first and second electrodes includes a distal end configured in a helical shape, and wherein the step of attaching the distal end of both of said first and second electrodes to a fiber includes wrapping the respective helically shaped electrode around said fiber.

17. The stimulation method of claim 14 wherein the step of attaching the distal end of at least one electrode to a fiber comprises attaching the distal end of both said first and second electrodes to the same fiber.

18. The stimulation method of claim 14 wherein the step of implanting said housing within said living tissue comprises implanting said tubular housing into the living tissue through the lumen of a needle.

19. The stimulation method of claim 14 further including implanting a plurality of said microdevices, each of said microdevices operating independent of the others, and controlling said plurality of microdevices so as to achieve a coordinated stimulation sequence therebetween.

20. An implantable microdevice of a size capable of insertion through the lumen of a hypodermic needle, said microdevice having a first coil and an electrical circuit, the first coil being positioned within the microdevice so that it may be inductively coupled With a non-implanted. Second coil through which power and control information nay be coupled to the electrical circuit through the first coil, the electrical circuit including means for generating an electrical stimulus, said microdevice having a wire electrode attached thereto through which said electrical stimulus may be delivered, said electrode being configured for attachment to a fiber within living tissue.

21. The implantable microdevice as set forth in claim 20 wherein said electrode comprises a helically formed wire adapted to anchor the microdevice in a given implant location.

22. The implantable microdevice as set forth in claim 21 wherein said electrical circuit further includes means for sensing biopotential signals and neural impulses and wherein said helically formed wire comprises a sensing electrode to sense biopotential signals or neural impulses associated with the fiber to which the electrode is attached.

* * * * *